United States Patent
Hall et al.

(10) Patent No.: US 10,159,820 B2
(45) Date of Patent: Dec. 25, 2018

(54) ANATOMICAL STRUCTURE ACCESS

(71) Applicant: Covidien LP, Mansfield, MA (US)

(72) Inventors: Rachel Hall, Quincy, MA (US); Raymond Avitable, Bourne, MA (US)

(73) Assignee: Covidien LP, Mansfield, MA (US)

( * ) Notice: Subject to any disclaimer, the term of this patent is extended or adjusted under 35 U.S.C. 154(b) by 255 days.

(21) Appl. No.: 15/084,622

(22) Filed: Mar. 30, 2016

(65) Prior Publication Data

US 2017/0281911 A1    Oct. 5, 2017

(51) Int. Cl.
| | |
|---|---|
| *A61M 25/00* | (2006.01) |
| *A61M 25/09* | (2006.01) |
| *A61B 17/34* | (2006.01) |
| *A61M 25/06* | (2006.01) |

(52) U.S. Cl.
CPC ... *A61M 25/09041* (2013.01); *A61B 17/3496* (2013.01); *A61B 17/3498* (2013.01); *A61M 25/0606* (2013.01); *A61M 25/0618* (2013.01)

(58) Field of Classification Search
CPC .......... A61M 25/0606; A61M 25/0618; A61M 25/0631; A61M 25/0637
See application file for complete search history.

(56) References Cited

U.S. PATENT DOCUMENTS

| | | | | |
|---|---|---|---|---|
| 3,388,703 | A * | 6/1968 | Bowes .............. | A61M 25/0606 604/166.01 |
| 5,295,970 | A | 3/1994 | Clinton et al. | |
| 6,027,480 | A * | 2/2000 | Davis ................ | A61M 25/0606 604/164.05 |
| 8,262,671 | B2 * | 9/2012 | Osypka ............ | A61M 25/0097 606/1 |
| 8,412,300 | B2 | 4/2013 | Sonderegger | |
| 8,496,610 | B2 | 7/2013 | Levenson et al. | |
| 8,882,713 | B1 | 11/2014 | Call et al. | |
| 2004/0167444 | A1 | 8/2004 | Laroya et al. | |
| 2004/0181150 | A1 | 9/2004 | Evans et al. | |
| 2007/0093778 | A1 * | 4/2007 | Cindrich ............... | A61M 5/158 604/500 |
| 2008/0215006 | A1 * | 9/2008 | Thorkild .......... | A61M 5/14248 604/151 |

(Continued)

FOREIGN PATENT DOCUMENTS

| | | | | |
|---|---|---|---|---|
| WO | WO/2015/024904 | * | 2/2015 | ............ A61M 25/00 |
| WO | 2015164131 | A1 | 10/2015 | |

OTHER PUBLICATIONS

International Search Report and Written Opinion from International Application No. PCT/US2017/024694, dated Jul. 14, 2017, 14 pp.

*Primary Examiner* — Scott Medway
(74) *Attorney, Agent, or Firm* — Kenneth Collier; Jessica Kwak Rauckman

(57) ABSTRACT

A method of accessing a hollow anatomical structure (HAS) of a patient includes puncturing the patient's skin with a needle, upon which is disposed a cannula. A tip portion of the needle is inserted into the HAS. A distal portion of the cannula is advanced distally along the needle, until the distal portion of the cannula is in the HAS. The needle is removed from the HAS while the distal portion of the cannula remains in the HAS. A guide wire is inserted into the HAS via the cannula. The cannula is removed from the HAS while at least a portion of the guide wire remains in the HAS.

22 Claims, 10 Drawing Sheets

(56) References Cited

U.S. PATENT DOCUMENTS

| | | | | |
|---|---|---|---|---|
| 2009/0187147 A1* | 7/2009 | Kurth | ............... | A61M 25/0606 |
| | | | | 604/161 |
| 2014/0214005 A1 | 7/2014 | Belson | | |
| 2015/0011977 A1* | 1/2015 | Kuniyasu | .............. | A61M 39/10 |
| | | | | 604/507 |
| 2016/0100860 A1* | 4/2016 | Lenker | ............... | A61B 17/3478 |
| | | | | 604/95.01 |
| 2016/0331935 A1* | 11/2016 | Saatchi | ............. | A61M 25/0606 |

* cited by examiner

ANATOMICAL STRUCTURE ACCESS

BACKGROUND

Generally, access devices are used to provide fluid communication with a patient's internal anatomy. For example, a catheter may be used to deliver fluid to the patient's vasculature or to withdraw fluid from the patient's vasculature. Currently, a clinician must perform a series of preliminary steps in order to place the catheter in communication with the patient's vasculature. For instance, an initial access step is performed by puncturing the patient's skin with a micro-access needle. A micro guide wire is then inserted into the micro-access needle and into the patient's vasculature. The micro-access needle is withdrawn over the micro guide wire leaving the micro guide wire in place. Next, a rigid dilator is advanced over the micro guide wire to expand the access pathway. The micro guide wire is removed and a larger size guide wire is inserted into the dilator. The dilator can then be removed leaving the larger guide wire for use by the clinician to advance a catheter into the patient's vasculature. Once the desired device is in place in the patient's vasculature, the larger guide wire can be removed. One problem with this conventional vascular access procedure, however, is that the use of the rigid dilator can cause significant patient trauma.

SUMMARY

The present disclosure is directed to a method and kit for accessing a hollow anatomical structure of a patient with reduced patient trauma, as compared to conventional vascular access procedures that use dilators.

In one aspect, a method of accessing a hollow anatomical structure (HAS) of a patient includes puncturing the patient's skin with a needle, upon which is disposed a cannula. A tip portion of the needle is inserted into the HAS. A distal portion of the cannula is advanced distally along the needle, until the distal portion of the cannula is in the HAS. The needle is removed from the HAS while the distal portion of the cannula remains in the HAS. A guide wire is inserted into the HAS via the cannula. The cannula is removed from the HAS while at least a portion of the guide wire remains in the HAS.

In some embodiments, a catheter is advanced over the guide wire and into the HAS.

In other embodiments, the needle defines a needle longitudinal axis and the cannula defines a cannula longitudinal axis. The cannula is disposed on the needle such that the cannula longitudinal axis is coaxially aligned with the needle longitudinal axis.

In some embodiments, the distal portion of the cannula is advanced along the needle longitudinal axis and the needle is moved in a proximal direction along the cannula longitudinal axis.

In other embodiments, the guide wire is moved in a distal direction along the cannula longitudinal axis.

In some embodiments, the cannula comprises a port. The needle and guide wire are moved through the port.

In other embodiments, the cannula longitudinal axis intersects the port.

In some embodiments, the port is a hemostatic valve.

In other embodiments, the hemostatic valve maintains the position of the guide wire in the HAS.

In some embodiments, the cannula is less rigid than the needle.

In other embodiments, the tip portion of the needle extends distally of the distal portion of the cannula while the needle punctures the patient's skin and while the tip portion of the needle is inserted into the HAS.

In some embodiments, the cannula defines a lumen having an inner diameter greater than an outer diameter of the needle and the lumen of the cannula is moved along the outer diameter of the needle.

In other embodiments, the guide wire is moved through the lumen of the cannula.

In another aspect, a kit includes a needle, a flexible cannula, a guide wire, and a package containing the needle, cannula, and guide wire. The flexible cannula includes a distal portion and a proximal portion. The cannula defines a lumen extending from the proximal portion to the distal portion. The needle is disposed in the lumen. The needle includes a tip portion extending distally beyond the distal portion of the cannula. The needle is movable in a proximal direction for removal from the cannula at the proximal portion of the lumen. The guide wire is movable through the lumen from the proximal portion to the distal portion of the cannula.

In some embodiments, the needle defines a needle longitudinal axis and the lumen of the cannula defines a cannula longitudinal axis. The needle longitudinal axis is coaxially aligned with the cannula longitudinal axis when the needle is disposed in the lumen.

In other embodiments, the cannula includes a port disposed along the proximal portion of the cannula. The needle is movable through the port for removal from the cannula at the proximal portion of the lumen.

In some embodiments, the guide wire is movable through the port and into the lumen of the cannula.

In other embodiments, the cannula longitudinal axis intersects the port.

In some embodiments, the port is a hemostatic valve.

Embodiments can include one or more of the following advantages.

In some embodiments, access to an anatomical structure of a patient is achieved with significantly less trauma to the patient. Additionally, access is achieved without the use of a dilator.

In other embodiments, access to an anatomical structure of a patient is achieved through minimal access steps.

In some embodiments, access to an anatomical structure of a patient is achieved with a single access device and a guide wire.

Other aspects, features, and advantages will be apparent from the description and drawings, and from the claims.

DETAILED DESCRIPTION

Figure 1:
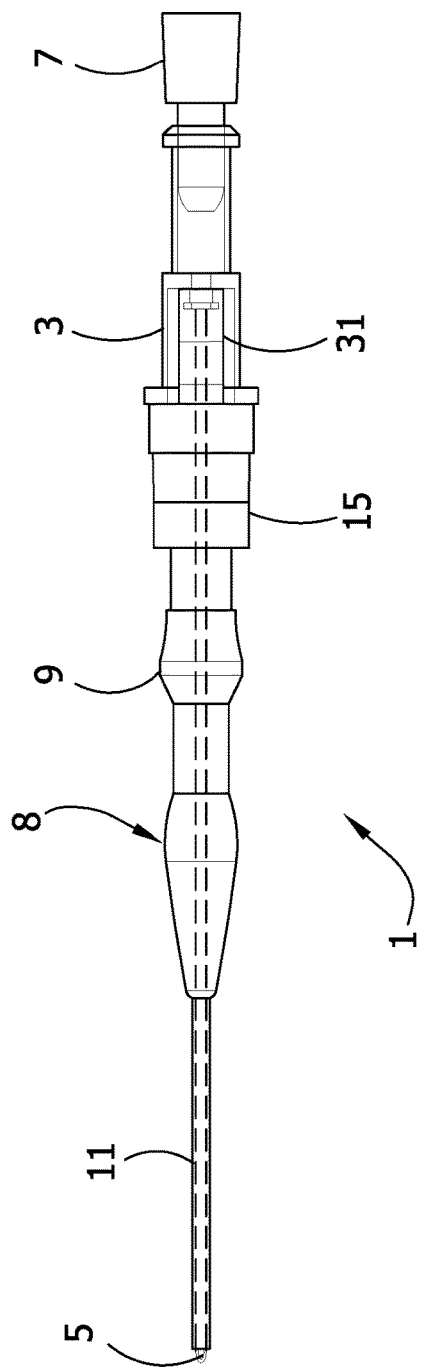
FIG. 1 is a side elevation of an access device.
Figure 2:
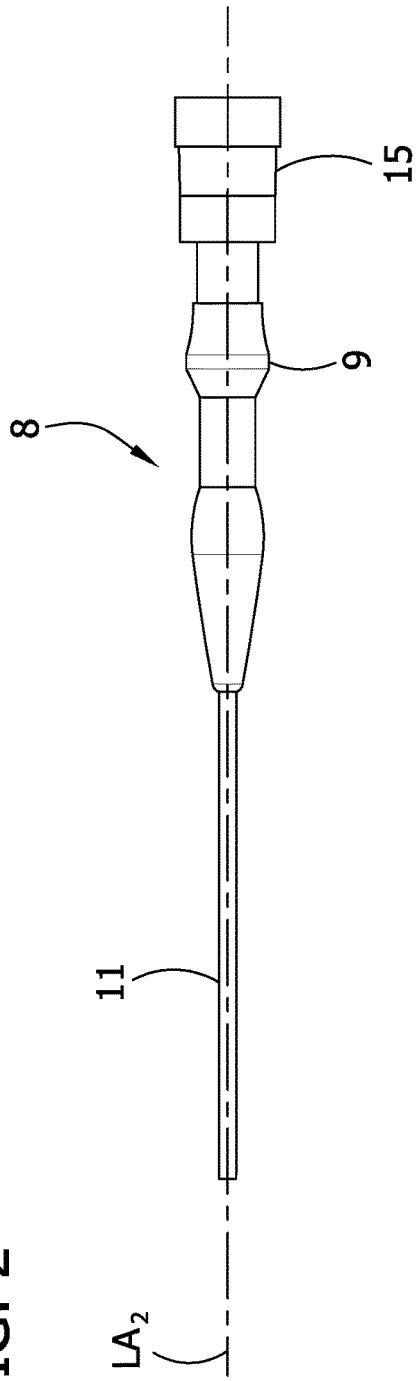
FIG. 2 is the side elevation of the access device of FIG. 1 with a needle and needle hub removed.
Figure 3:
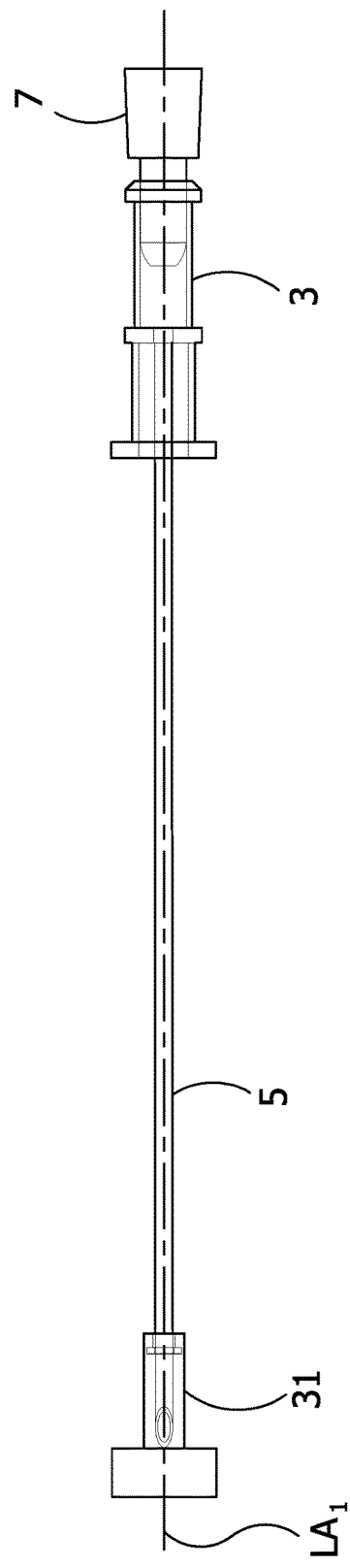
FIG. 3 is a side elevation of the needle and needle hub with a needle-stick prevention mechanism disposed over the needle.
Figure 8:
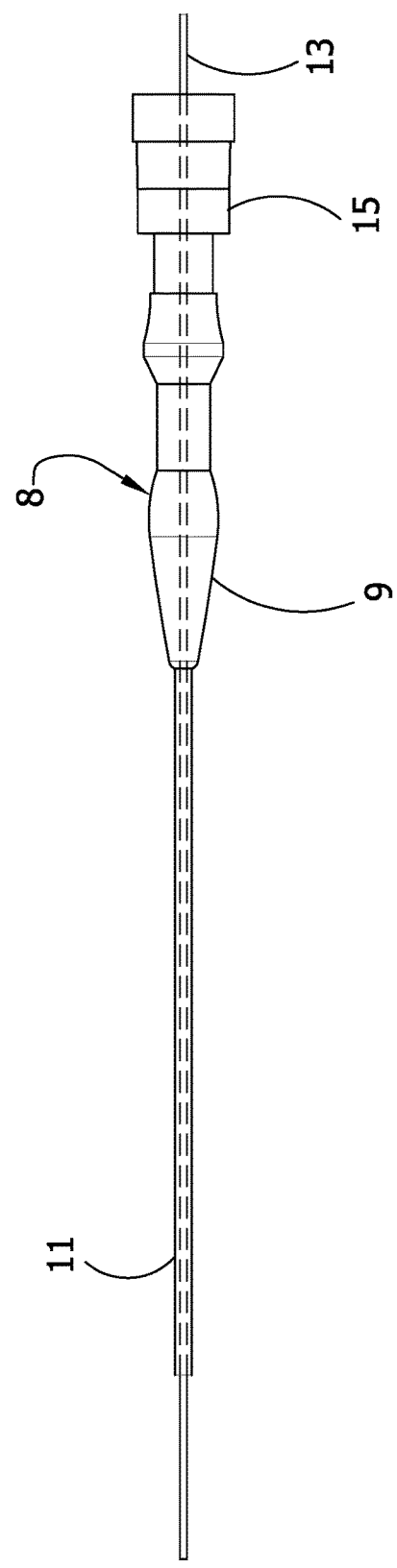
FIG. 8 is an illustration of a guide wire inserted in the access device.

Referring to FIGS. 1-4, an access device 1 includes a needle hub 3 and a needle shaft 5 fixedly attached to the needle hub at a proximal end of the needle shaft. A plug 7 is disposed in a proximal end of the needle hub 3. The needle shaft 5 extends distally from the needle hub to a sharp distal tip. When the access device 1 is in a pre-use configuration, a cannula 8 including a cannula hub 9 and a flexible tube 11, extending distally from the cannula hub, surrounds at least a portion of the needle shaft 5. At least a portion of the sharp distal tip of the needle shaft 5 extends past a distal end of the cannula 8 so that the sharp distal tip can be used to puncture a subject's skin during use. The needle shaft 5 defines a needle longitudinal axis $LA_2$ (FIG. 3), and the cannula 8 defines a cannula longitudinal axis $LA_2$ (FIG. 2). In certain embodiments, the cannula 8 is disposed on the needle shaft 5 such that the cannula longitudinal axis $LA_2$ is coaxially aligned with the needle longitudinal axis $LA_1$. The cannula 8 defines a lumen extending from a proximal portion of the cannula to a distal portion of the cannula. The lumen of the cannula 8 has an inner diameter that is greater than an outer diameter of the needle shaft 5. Therefore, the cannula 8 can move (e.g., longitudinally and/or rotationally) along an outer surface of the needle shaft 5 as will be explained in greater detail below. A guide wire 13 is insertable into the access device 1 (FIG. 8). The access device 1 and guide wire 13 are used to gain access to a hollow anatomical structure (HAS) of a patient such as a vein V to provide a guide for inserting a catheter C (FIG. 13) into the vein.

The needle shaft 5 and cannula 8 facilitate access of a patient's vein or other HAS with minimal stress to the patient's tissue. In particular, the access device 1, including the needle shaft 5 and cannula 8, provides a single access assembly which can be used, with the guide wire 13, to gain access to the patient's HAS thereby limiting the number of devices and steps needed to access the patient's HAS. Additionally, the access device 1 provides access to the patient's HAS without the use of a rigid dilator which can be stressful on the patient's tissue causing significant trauma to the patient. As a result, the access device 1 facilitates access to the patient's HAS with less resulting trauma to the patient.

Figure 4:
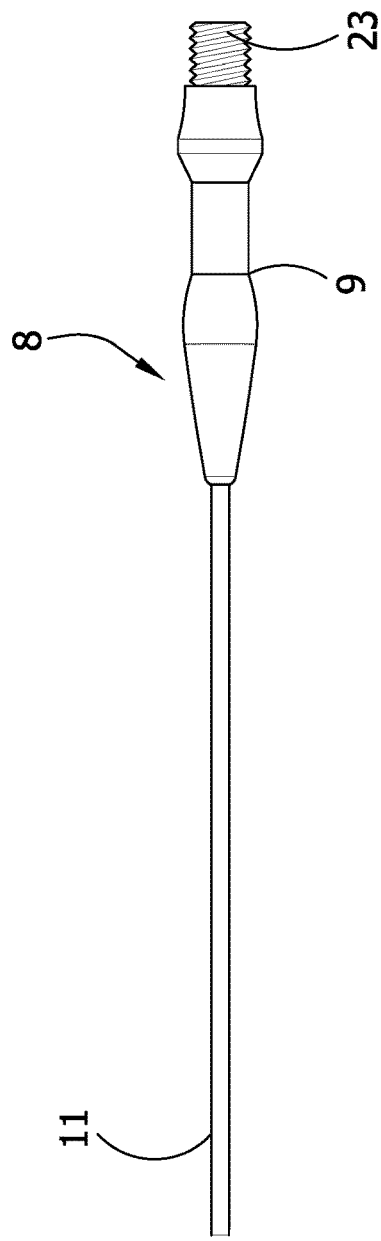
FIG. 4 is the side elevation of FIG. 2 with a valve of the access device removed.
Figure 5:
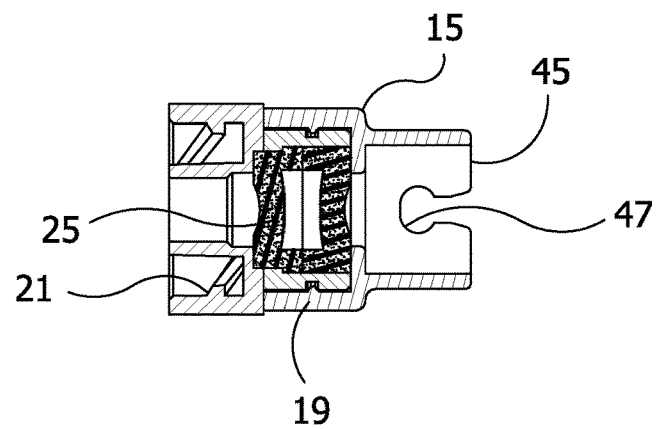
FIG. 5 is a horizontal cross section of the valve.

Referring to FIGS. 2, 4, and 5, a hemostatic valve 15 is removably attached to a proximal end of the cannula hub 9. The valve 15 defines a port of the cannula 8 when attached to the cannula hub 9. The valve 15 includes a housing 19 including threads 21 that mate with threads 23 on the cannula hub 9. For example, the threads 21 of the housing and the threads on the cannula 9 can be mating portions of a Luer lock connection.

The access device 1 has an axial alignment such that the longitudinal axis $LA_2$ of the cannula 8, and the longitudinal axis $LA_1$ of the needle shaft 5 when the needle shaft is received in the cannula 8, extend through the port and through the valve 15. A valve member 25 is hemostatic and prevents a backflow of blood out of the port of the cannula 8 when the valve is attached to the port. The valve member 25 also seals around the needle shaft 5. Therefore, as the needle shaft 5 is moved with respect to the cannula 8, fluid is prevented from escaping the access device 1 around an outer surface of the needle shaft. In some embodiments, the valve 15 comprises a "gummy" valve. In certain embodiments, the valve 15 positions the needle shaft 5 as the needle is moved with respect to the cannula hub 9 and flexible tube 11. For instance, the valve 15 may yieldably resist movement of the needle shaft 5 along the longitudinal axis $LA_2$ of the cannula 8.

Figure 6:
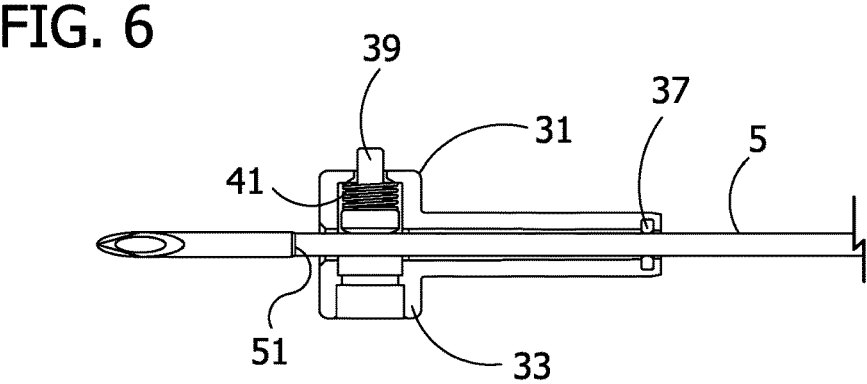
FIG. 6 is an illustration of the needle in an unprotected configuration.
Figure 7:
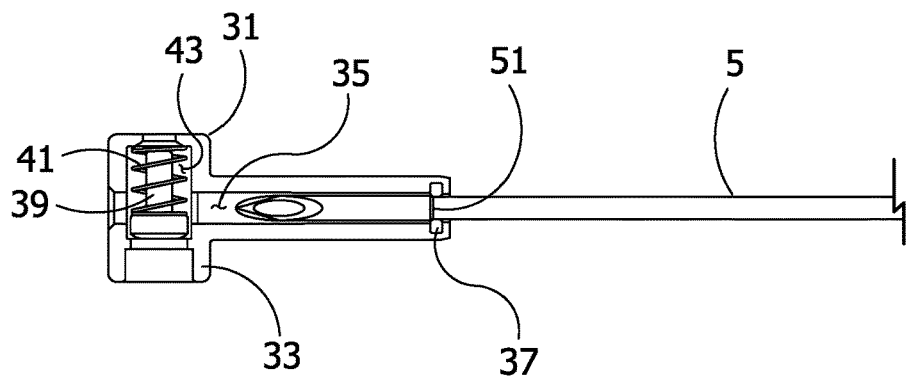
FIG. 7 is an illustration of the needle in a protected configuration.

Referring to FIGS. 6 and 7, a needle-stick prevention mechanism 31 is releasably secured to the housing 19 of the valve 15. The needle-stick prevention mechanism 31 comprises a main body 33 having a proximal portion and a distal portion. A needle passage 35 (FIG. 7) extends through the proximal and distal portions of the main body 33. A retaining ring 37 is disposed in the needle passage in the proximal portion of the main body 33. The distal portion of the main body 33 at least partially houses a blocking arm 39 biased by a spring 41 and movable in a transverse passage 43 in the distal portion of the main body. In the pre-use configuration, the needle shaft 5 passes entirely through the needle passage 35 in the main body 33 of the needle-stick prevention mechanism 31. In this configuration, the needle shaft 5 holds the blocking arm 39, against the bias of the spring 41, to one side of the distal portion of the main body 33 (FIG. 6). As a result, an end of the blocking arm 39 extends out of the transverse passage 43.

The distal portion of the main body 33 of the needle-stick prevention mechanism 31 is received in an open end 45 of the housing 19 of the valve 15 in the pre-use configuration (FIGS. 1 and 5). In particular, the end of the blocking arm 39 that extends out of the transverse passage 43 is received in a recess 47 in the housing 19 of the valve 15. A diameter of the end of the blocking arm 39 is sized larger than a narrow section of the recess 47 so that the needle-stick prevention mechanism 31 is prevented from being pulled out of the valve housing 19.

The needle hub 3 and needle shaft 5 are movable relative to the cannula 8, hemostatic valve 15, and needle-stick prevention mechanism 31 to withdraw the needle shaft 5 from the cannula and valve after the subject's skin has been punctured and the cannula has been placed in communication with the subject's HAS. If the sharp distal tip of the needle shaft 5 is withdrawn proximally of the blocking arm 39 of the needle-stick prevention mechanism 31, the bias of the spring 41 causes the blocking arm to move along the transverse passage 43, across the needle passage 35, blocking the needle passage. This movement also moves the end of the blocking arm 39 out of the recess 47 in the valve 15 allowing the needle-stick prevention mechanism 31 to be separated from the valve (FIG. 7). Thus, the blocking arm 39 prevents the sharp distal tip of the needle shaft 5 from being moved distally out of the main body 33 of the needle-stick prevention mechanism 31. A crimp 51 on the needle shaft 5 is engageble with the retaining ring 37 in the proximal portion of the main body 33 of the needle-stick prevention mechanism 31. Therefore, the retaining ring 37 prevents the sharp distal tip of the needle shaft 5 from being moved proximally out of the main body 33 of the needle-stick prevention mechanism 31. Accordingly, the sharp distal tip of the needle shaft 5 is enclosed in the main body 33 of the needle-stick prevention mechanism 31 preventing the chance of an accidental stick by the needle once it has been pulled out of the cannula 8 and hemostatic valve 15.

Figure 9:
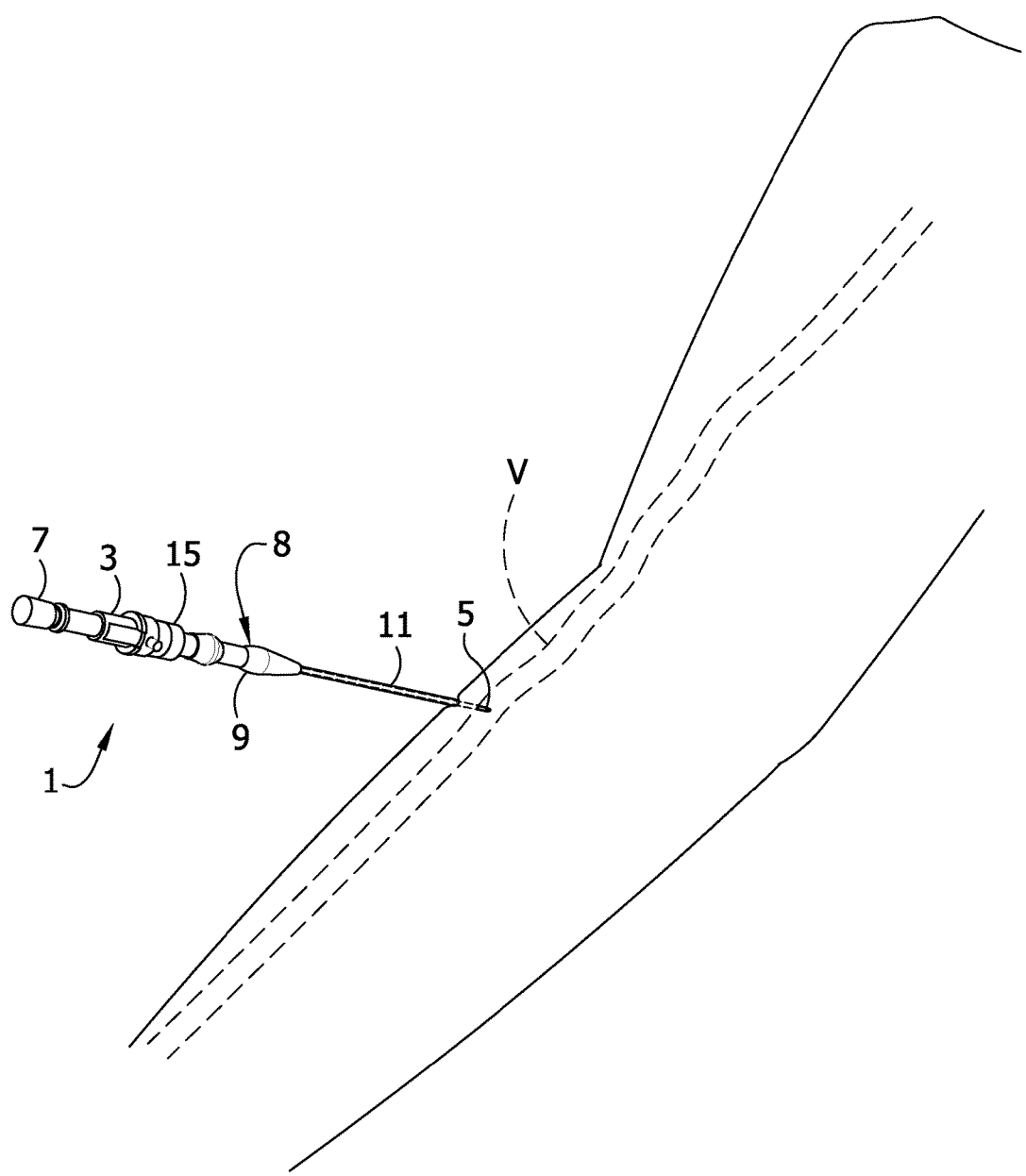
FIGS. 9-13 are schematic illustrations of a process of using the access device to access a patient's hollow anatomical structure.
Figure 10:
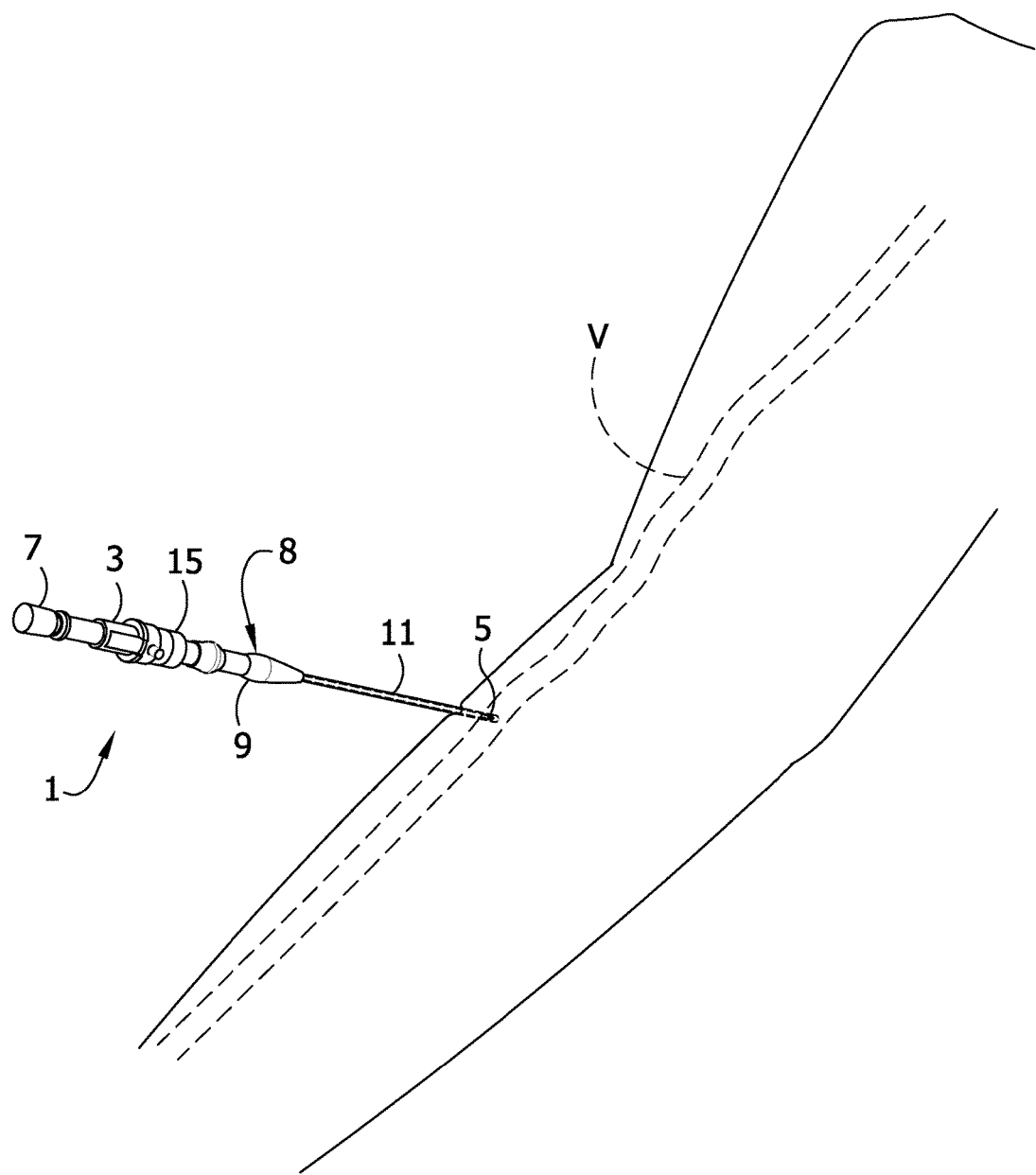
Figure 11:
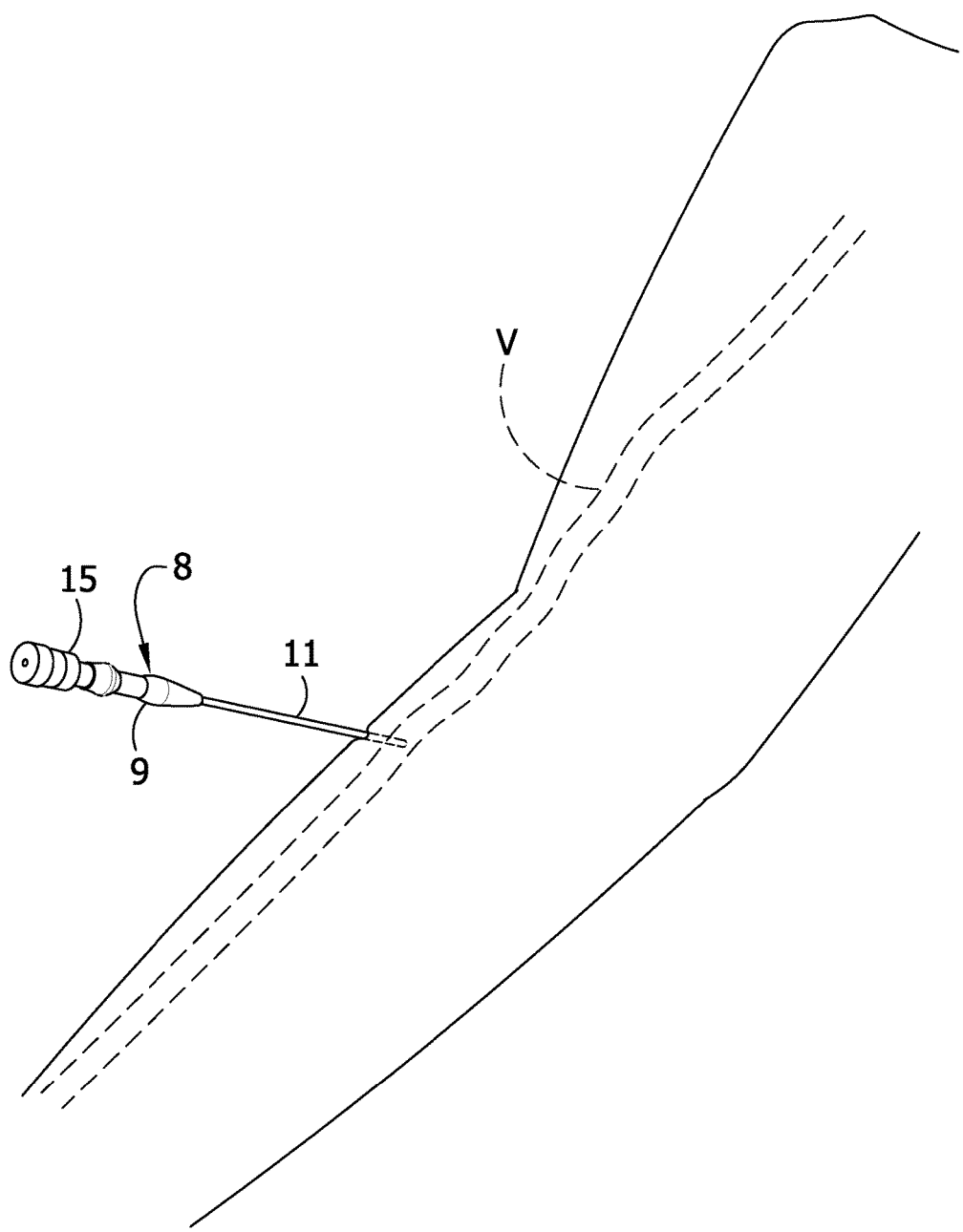

In use, referring to FIGS. 9-13, the access device 1 is positioned near the patient's skin at a location of the HAS that is to be accessed. The patient's skin is then punctured with the sharp distal tip of the needle shaft 5 at the location of the HAS. The distal tip of the needle shaft 5, along with the cannula 8 disposed on the needle shaft, is inserted into the patient's HAS (FIG. 9). In the illustrated embodiment, the HAS is a vein V. The lumen of the cannula 8 is moved along the outer diameter of the needle shaft to advance the flexible tube 11 of the cannula 8 distally along the needle shaft 5. More particularly, in order to place the flexible tube 11 in the patient's vein V, the cannula 8 is moved distally along the needle shaft 5 shaft such that a distal end of the flexible tube is moved over the distal tip of the needle shaft and into the patient's vein V (FIG. 10). In some embodiments, the cannula 8 is moved distally along the longitudinal axis $LA_1$ of the needle shaft 5. Next, the needle shaft 5 is moved proximally with respect to the cannula 8 to withdraw the needle shaft from the patient's vein V and to withdraw the needle shaft from the cannula (FIG. 11). With the needle removed, the valve 15 prevents a backflow of blood out of the cannula 8. In certain embodiments, the needle shaft 5 is moved proximally along the cannula longitudinal axis $LA_2$. In some embodiments, the needle shaft 5 is withdrawn from the port of the cannula 8.

Figure 12:
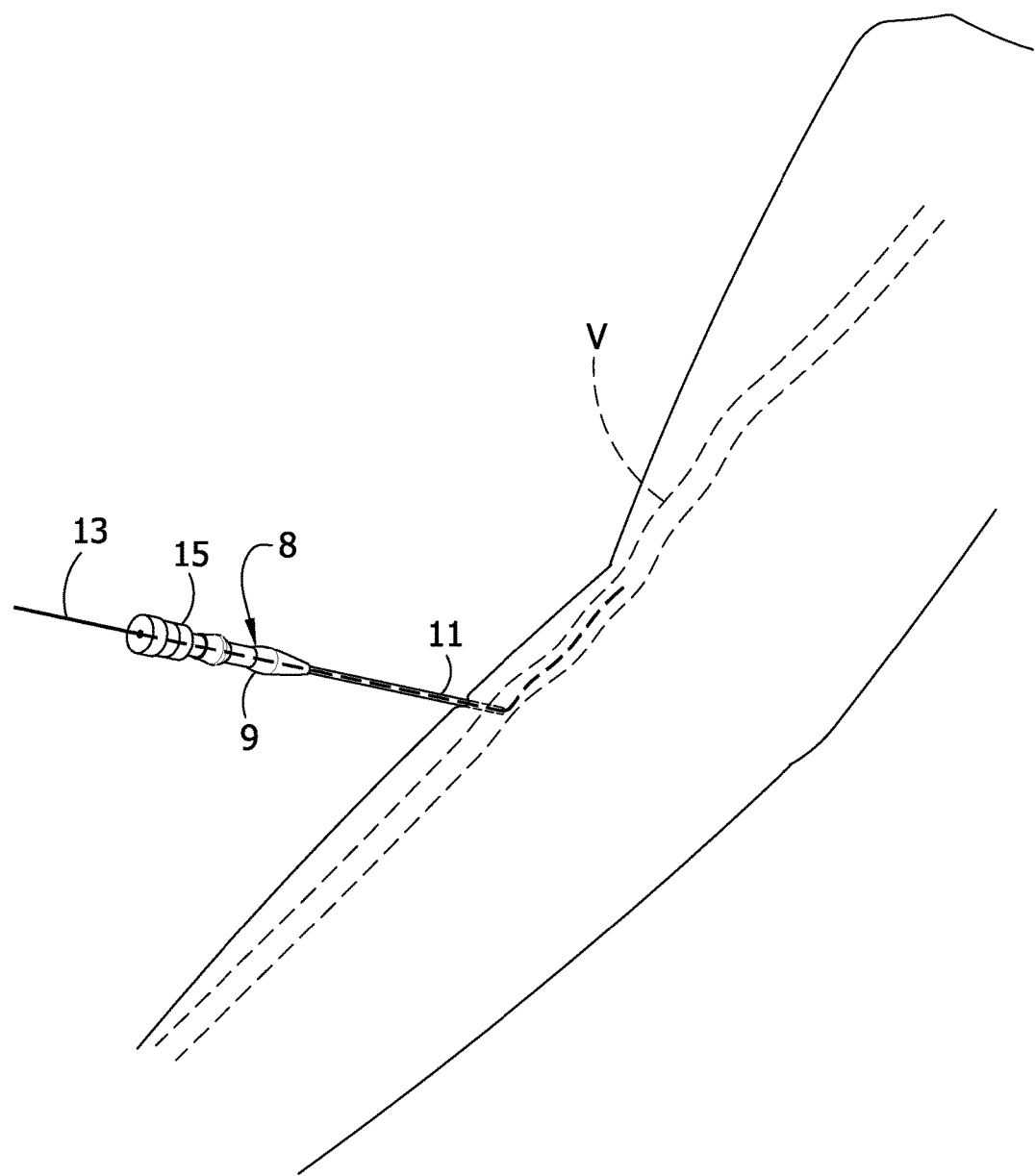
Figure 13:
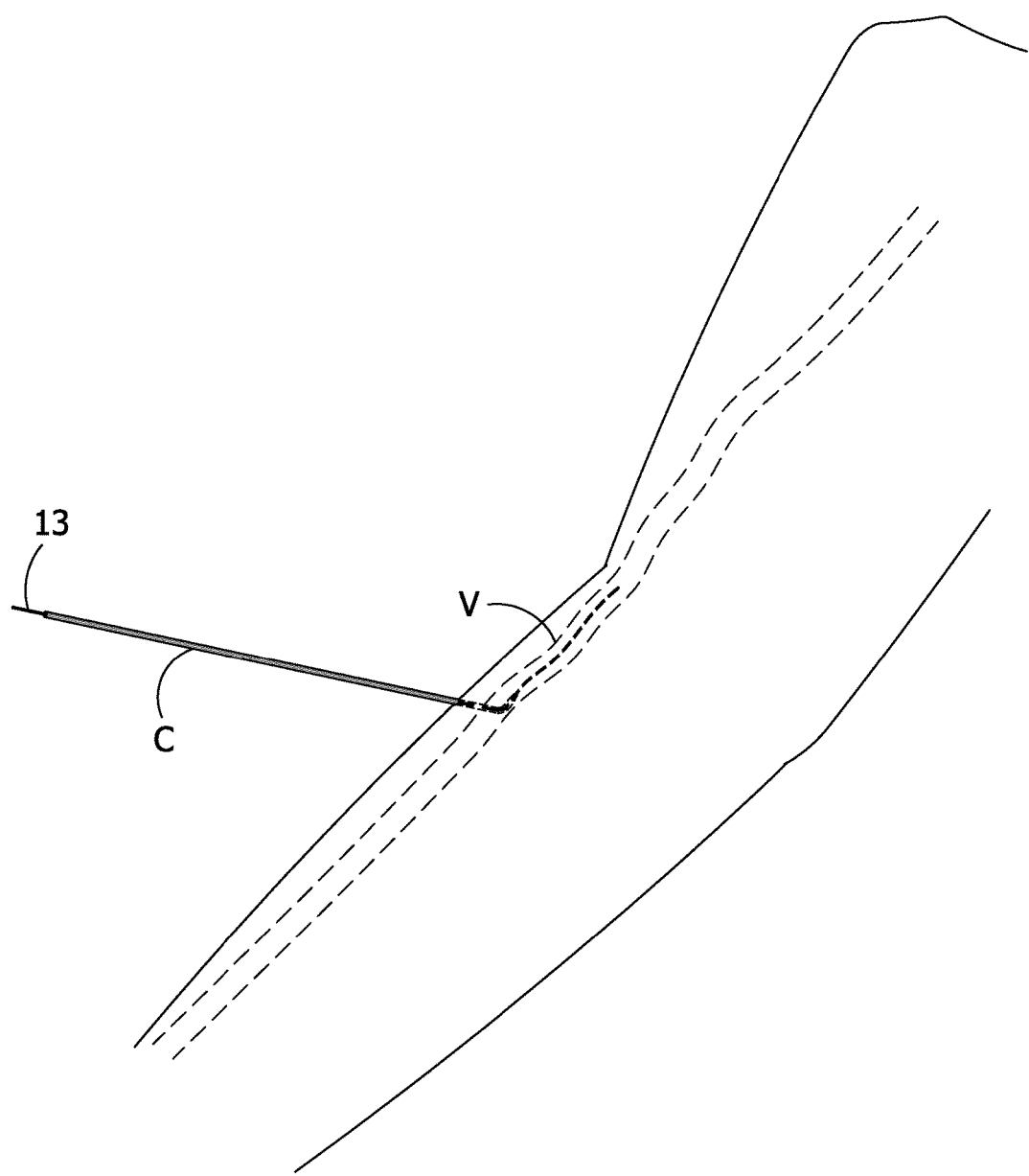

Referring to FIG. 12, the guide wire 13 is then inserted through the valve 15 at the port and into the cannula 8. Continued insertion of the guide wire 13 passes the guide wire through the cannula hub 9, through the flexible tube 11, and into the patient's vein V. The valve 15 functions to maintain a position of the guide wire 13. For instance, the valve 15 holds the guide wire 13 in place in the patient's vein V. The flexible tube 11 can be removed from the patient's vein V once the guide wire 13 is in place in the patient's vein. Movement of the flexible 11 and cannula hub 9, proximally away from the patient's vein V will remove the cannula 8 from the guide wire 13 completely (FIG. 13). The guide wire 13 is then in position for guiding a medical device into the patient's vein V. For instance, a catheter C can be advanced over the guide wire 13 and into the patient's vein V.

This process facilitates access to the patient's HAS using only the access device 1 and the guide wire 13. Thus, the process for facilitating access to the HAS is simplified and uses less components. As a result, the trauma to the patient's body is lessened.

In some embodiments, the needle shaft 5 is made from a rigid material such as stainless steel. In other embodiments, the needle shaft 5 is a 19 gauge needle. In some embodiments, the needle shaft is a 21 gauge needle.

In other embodiments, the flexible tube 11 of the cannula 8 is made from a flexible material, such as polypropylene, which is less rigid than the needle shaft 5. In some embodiment, the flexible tube 11 is a 17 gauge cannula. In other embodiments, the flexible tube 11 is a 19 gauge cannula. Use of the flexible tube 11 to place the guide wire 13 in the patient's HAS is believed to lessen the trauma to the patient as compared to the use of a rigid dilator.

In other embodiments, a ratio of an outer diameter of the flexible tube 11 of the cannula 8 to an outer diameter of the needle shaft 5 is between about 1.6 to 1 and about 1.2 to 1. In some embodiments, the outer diameter of the flexible tube 11 is about 0.056 inches (1.422 mm). It is believed that the ratio of outer diameters of the flexible tube 11 and needle shaft 5 is relatively small so that the transition between inserting the needle into the patient's HAS and then moving the cannula over the needle and into the patient's HAS provides minimal stress on the patient's tissue resulting in a less traumatic access process.

In some embodiments, the guide wire 13 has an outer diameter of about 0.018 in. (0.457 mm).

Figure 14:
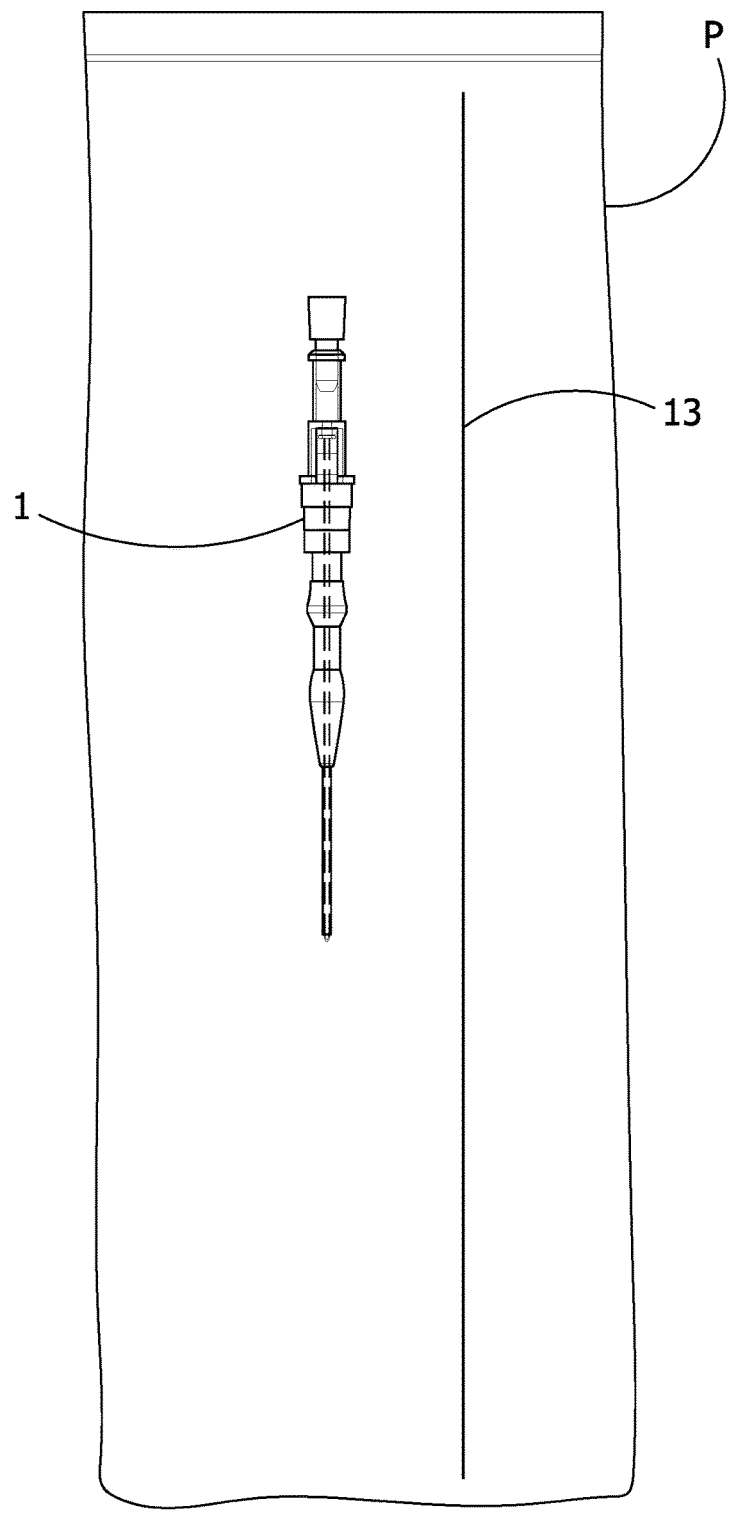
FIG. 14 is an illustration of the access device and guide wire in a package.

In certain embodiments, the access device 1 and guide wire 13 come pre-packaged in a package P to facilitate use of the access device (FIG. 14). In the package P, the access device 1 is configured in its pre-use configuration where the needle shaft 5 is disposed within the lumen of the cannula 8 such that the sharp distal tip of the needle shaft extends distally of the distal end of the cannula. The guide wire 13 is packaged with the access device 1 but is not inserted into the cannula 8 within the package. However, the guide wire 13 is configured for movement through the lumen of the cannula 8 during use of the access device 1.

While certain embodiments have been described, other embodiments are additionally or alternatively possible.

A number of embodiments have been described. Nevertheless, it will be understood that various modifications may be made without departing from the spirit and scope of the disclosure. Accordingly, other embodiments are within the scope of the following claims.

What is claimed is:

1. A method of accessing a hollow anatomical structure (HAS) of a patient, the method comprising:
   puncturing skin of the patient with a needle, upon which is disposed a cannula including a distal portion and a proximal portion, the cannula defining a lumen extending from the proximal portion to the distal portion, wherein when the needle is disposed in the lumen in a deployed configuration, a tip portion of the needle extends distally beyond the distal portion of the cannula,
   wherein a valve is attached to a proximal end of the cannula, the valve being configured to form a seal around the needle when the needle is disposed in the lumen, and
   wherein a needle-stick prevention mechanism is mechanically connected to the valve, the needle-stick prevention mechanism defining a needle passage configured to receive the needle and comprising a blocking member movable between a first position and a second position, wherein the blocking member is in the first position when the tip portion of the needle extends distal to the blocking member,
   wherein the valve defines a recess configured to receive the blocking member when the blocking member is in the first position to mechanically connect the needle-stick prevention mechanism and the valve;
   inserting a tip portion of the needle into the HAS;
   advancing a distal portion of the cannula distally along the needle, until the distal portion of the cannula is in the HAS;
   removing the needle from the HAS while the distal portion of the cannula remains in the HAS, wherein removing the needle from the HAS comprises withdrawing the needle from the cannula proximally and removing the needle from the lumen at the proximal portion of the lumen, wherein upon moving the tip portion of the needle proximal to the blocking member, the blocking member moves to the second position in which the blocking member is disposed within the needle passage and blocks movement of the needle distally past the blocking member;
   inserting a guide wire into the HAS via the cannula; and
   removing the cannula from the HAS while at least a portion of the guide wire remains in the HAS.

2. The method of claim 1, further comprising advancing a catheter over the guide wire and into the HAS.

3. The method of claim 1, wherein the needle defines a needle longitudinal axis, the cannula defines a cannula longitudinal axis, and the cannula is disposed on the needle such that the cannula longitudinal axis is coaxially aligned with the needle longitudinal axis.

4. The method of claim 3, wherein advancing a distal portion of the cannula distally along the needle includes advancing the distal portion of the cannula along the needle longitudinal axis and removing the needle from the HAS includes moving the needle in a proximal direction along the cannula longitudinal axis.

5. The method of claim 4, wherein inserting the guide wire into the HAS via the cannula includes moving the guide wire in a distal direction along the cannula longitudinal axis.

6. The method of claim 5, wherein removing the needle from the HAS further includes moving the needle through the valve and inserting the guide wire into the HAS via the cannula further includes moving the guide wire through the valve.

7. The method of claim 3, wherein the cannula longitudinal axis intersects the valve.

8. The method of claim 6, wherein the valve comprises a hemostatic valve.

9. The method of claim 8, wherein the hemostatic valve maintains the position of the guide wire in the HAS.

10. The method of claim 1, wherein the cannula is less rigid than the needle.

11. The method of claim 1, wherein the tip portion of the needle extends distally of the distal portion of the cannula while the needle punctures the patient's skin and while the tip portion of the needle is inserted into the HAS.

12. The method of claim 1, wherein the lumen of the cannula has an inner diameter greater than an outer diameter of the needle and advancing the distal portion of the cannula distally along the needle includes moving the lumen of the cannula along the outer diameter of the needle.

13. The method of claim 1, wherein inserting the guide wire into the HAS via the cannula includes moving the guide wire through the lumen of the cannula.

14. A kit comprising:
a flexible cannula including a distal portion and a proximal portion, the cannula defining lumen extending from the proximal portion to the distal portion;
a valve configured to attach to a proximal end of the cannula;
a needle configured to be disposed in the lumen, wherein the valve is configured to form a seal around the needle when the needle is disposed in the lumen, the needle comprising a tip portion configured to extend distally beyond the distal portion of the cannula when the needle is disposed in the lumen in a deployed configuration, and wherein the needle movable in a proximal direction for removal from the cannula at the proximal portion of the lumen;
a needle-stick prevention mechanism mechanically connected to the valve, the needle-stick prevention mechanism defining a needle passage configured to receive the needle and comprising a blocking member movable between a first position and a second position,
wherein the blocking member is in the first position when the tip portion of the needle extends distal to the blocking member, and when the blocking member is in the second position, the blocking member is disposed within the needle passage and blocks movement of the needle distally past the blocking member, and
wherein the valve defines a recess configured to receive the blocking member when the blocking member is in the first position to mechanically connect the needle-stick prevention mechanism and the valve;
a guide wire movable through the lumen from the proximal portion to the distal portion of the cannula; and
a package containing the needle, the cannula and the guide wire.

15. The kit of claim 14, wherein the needle defines a needle longitudinal axis and the lumen of the cannula defines a cannula longitudinal axis, the needle longitudinal axis coaxially aligned with the cannula longitudinal axis when the needle is disposed in the lumen.

16. The kit of claim 14, wherein the needle is movable through the valve for removal from the cannula at the proximal portion of the lumen.

17. The kit of claim 14, wherein the guide wire is movable through the valve and into the lumen of the cannula.

18. The kit of claim 15, wherein the cannula longitudinal axis intersects the valve.

19. The kit of claim 14, wherein the valve comprises a hemostatic valve.

20. The kit of claim 14, wherein the cannula is less rigid than the needle.

21. The kit of claim 14, wherein when the blocking member is in the second position, the blocking member is not received in the recess of the valve such that the needle-stick prevention mechanism is configured to be disconnected from the valve.

22. The method of claim 1, wherein when the blocking member moves to the second position, the blocking member is moved out of the recess of the valve such that the needle-stick prevention mechanism is configured to be disconnected from the valve, the method further comprising disconnecting the needle-stick prevention mechanism from the valve.

* * * * *